United States Patent
Jaax et al.

(10) Patent No.: US 8,060,209 B2
(45) Date of Patent: Nov. 15, 2011

(54) METHODS AND SYSTEMS OF TREATING ISCHEMIA PAIN IN VISCERAL ORGANS

(75) Inventors: Kristen N. Jaax, Santa Clarita, CA (US); Todd K. Whitehurst, Valencia, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 462 days.

(21) Appl. No.: 12/359,144

(22) Filed: Jan. 23, 2009

(65) Prior Publication Data

US 2009/0192570 A1 Jul. 30, 2009

Related U.S. Application Data

(60) Provisional application No. 61/023,499, filed on Jan. 25, 2008.

(51) Int. Cl.
*A61N 1/00* (2006.01)
(52) U.S. Cl. .......................................... 607/46
(58) Field of Classification Search .................. 607/46
See application file for complete search history.

(56) References Cited

U.S. PATENT DOCUMENTS

| | | | |
|---|---|---|---|
| 5,058,584 A * | 10/1991 | Bourgeois | 607/46 |
| 5,193,539 A | 3/1993 | Schulman et al. | |
| 5,193,540 A | 3/1993 | Schulman et al. | |
| 5,312,439 A | 5/1994 | Loeb | |
| 5,501,703 A | 3/1996 | Holsheimer et al. | |
| 5,938,688 A | 8/1999 | Schiff | |
| 6,016,449 A | 1/2000 | Fischell et al. | |
| 6,051,017 A | 4/2000 | Loeb et al. | |
| 6,058,331 A | 5/2000 | King | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,280,873 B1 | 8/2001 | Tsukamoto | |
| 6,381,496 B1 | 4/2002 | Meadows et al. | |
| 6,458,171 B1 | 10/2002 | Tsukamoto | |
| 6,463,328 B1 | 10/2002 | John | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,596,439 B1 | 7/2003 | Tsukamoto et al. | |
| 6,605,383 B1 | 8/2003 | Wu | |
| 6,607,843 B2 | 8/2003 | Ruth et al. | |
| 6,760,626 B1 | 7/2004 | Boveja | |
| 7,010,345 B2 * | 3/2006 | Hill et al. | 607/10 |
| 2003/0097159 A1 | 5/2003 | Schiff et al. | |
| 2006/0058854 A1 | 3/2006 | Abrams et al. | |
| 2007/0293908 A1 | 12/2007 | Cowan et al. | |
| 2008/0039904 A1 | 2/2008 | Bulkes et al. | |

FOREIGN PATENT DOCUMENTS

WO  WO-98/39357 A1  9/1998

(Continued)

*Primary Examiner* — George Manuel
(74) *Attorney, Agent, or Firm* — Frommer Lawrence & Haug LLP; Bruce E. Black

(57) ABSTRACT

Methods and systems of treating a patient with ischemia pain include providing a stimulator, configuring one or more stimulation parameters to treat ischemia pain in a visceral organ, programming the stimulator with the one or more stimulation parameters, generating a stimulus configured to treat ischemia pain with the stimulator in accordance with the one or more stimulation parameters, and applying the stimulus with the stimulator to one or more stimulation sites in accordance with the one or more stimulation parameters.

19 Claims, 13 Drawing Sheets

FOREIGN PATENT DOCUMENTS

| | | |
|---|---|---|
| WO | WO-99/20342 A1 | 4/1999 |
| WO | WO-99/55413 A1 | 11/1999 |
| WO | WO-2007/149936 A2 | 12/2007 |
| WO | WO-2008/019384 A1 | 2/2008 |

* cited by examiner

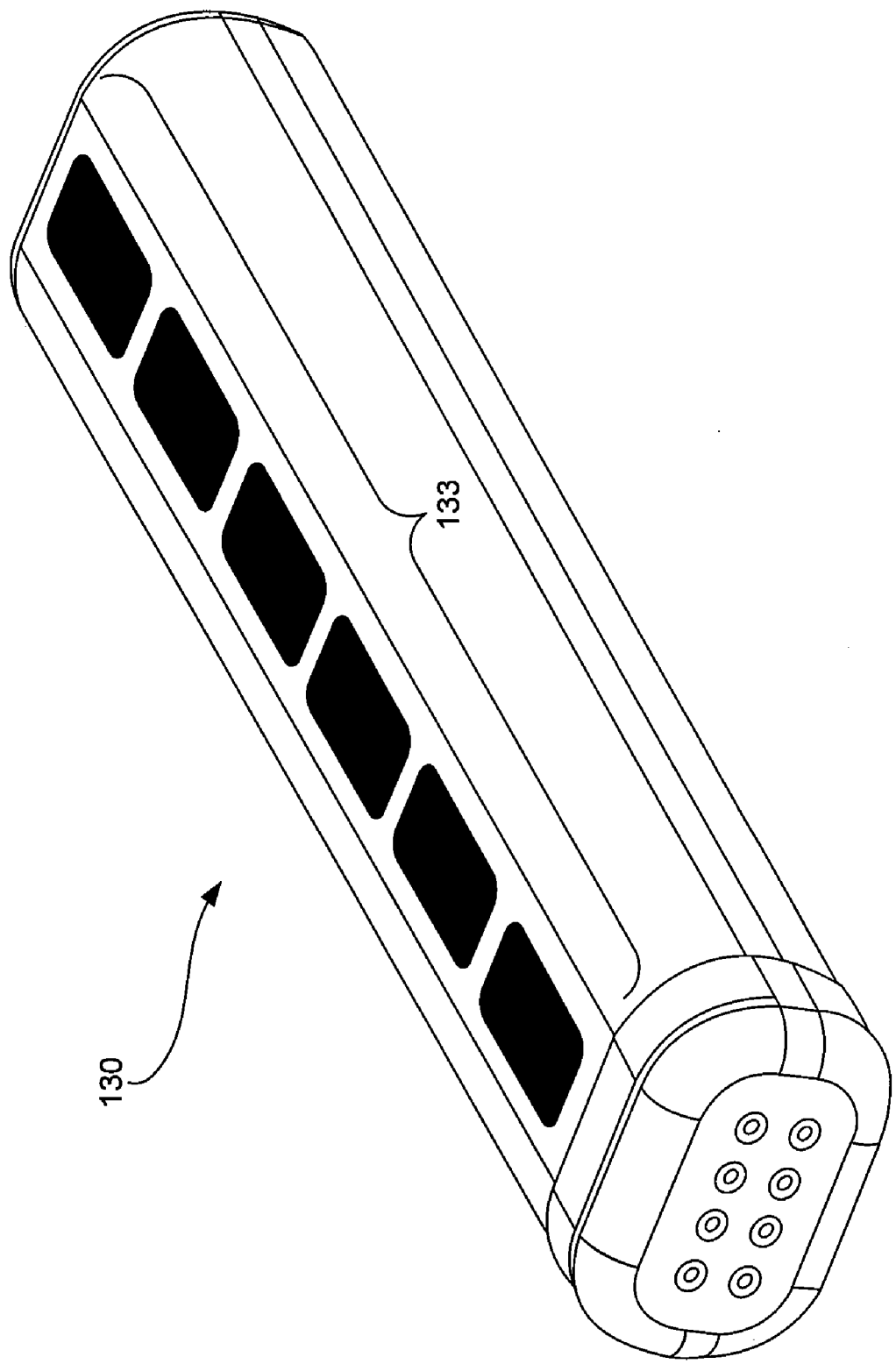

METHODS AND SYSTEMS OF TREATING ISCHEMIA PAIN IN VISCERAL ORGANS

CROSS-REFERENCE TO RELATED APPLICATIONS

The present application claims the benefit of U.S. Provisional Patent Application No. 61/023,499, filed Jan. 25, 2008, which is incorporated herein by reference in its entirety.

BACKGROUND

Visceral organs within humans and other mammals rely on the flow of blood to function properly. Exemplary visceral organs include, but are not limited to, the pancreas, duodenum, small intestine, colon, liver, spleen, kidneys, adrenal glands, stomach, appendix, and gall bladder, among others.

In some cases, a visceral organ may experience ischemia, which is a restriction or obstruction of blood flow to that organ. Ischemia in a visceral organ may potentially damage the organ, exacerbate an existing detrimental condition, and/or cause pain.

An exemplary cause of ischemia is chronic pancreatitis. Chronic pancreatitis is an inflammatory condition that results in permanent structural changes in the pancreas. Clinical manifestations of this disorder include chronic abdominal pain and pancreatic exocrine and endocrine dysfunction.

One theory regarding the pathogenesis of chronic pancreatitis suggests that increased secretion of pancreatic proteins causes proteinaceous plugs to form within the interlobular and intralobular ducts of the pancreas. These plugs may acts as a nidus for calcification, leading to stone formation within the duct system. The net result is the formation of ductal epithelial lesions which scar and obstruct the pancreatic ducts, thereby causing inflammatory changes and cell loss.

When a patient suffers from a pancreatic or biliary duct obstruction, such as those associated with pancreatitis, the outflow of pancreatic secretions may be obstructed, thus causing increased intraductal pressure. This rise in intraductal pressure may induce or contribute to pancreatic ischemia, which may be a major factor in pain experienced by patients with chronic pancreatitis.

Pancreatic ischemia is typically treated by surgically decompressing ducts within the pancreas using a procedure known as a Puestow procedure. During a Puestow procedure, the abdomen is opened with an incision extending from the lower breastbone to the umbilicus. The pancreas is exposed and the main pancreatic duct is opened. The opened pancreatic duct is then connected to a loop of small intestine so that the pancreas drains directly into the intestines. This procedure is highly invasive and irreversibly reconstructs the organs of the gastrointestinal system. In addition, 11% to 56% of patients do not achieve adequate pain relief with initial operative treatment, and subsequent operations for recurring or persistent pain are common.

SUMMARY

Methods of treating a patient with ischemia pain include providing a stimulator, configuring one or more stimulation parameters to treat ischemia pain in a visceral organ, programming the stimulator with the one or more stimulation parameters, generating a stimulus configured to treat ischemia pain with the stimulator in accordance with the one or more stimulation parameters, and applying the stimulus with the stimulator to at least one or more of a vascular tissue of the visceral organ and a nerve innervating the vascular tissue of the visceral organ in accordance with the one or more stimulation parameters.

Systems for treating a patient with ischemia pain include a stimulator configured to generate at least one stimulus in accordance with one or more stimulation parameters adjusted to treat ischemia pain in a visceral organ, a programmable memory unit in communication with the stimulator and programmed to store the one or more stimulation parameters to at least partially define the stimulus such that the stimulus is configured to treat the ischemia pain, and means, operably connected to the stimulator, for applying the stimulus to at least one or more of a vascular tissue of the visceral organ and a nerve innervating the vascular tissue of the visceral organ.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 4B shows an example of a microstimulator with a plurality of electrodes disposed on an outer surface thereof according to principles described herein.

Throughout the drawings, identical reference numbers designate similar, but not necessarily identical, elements.

DETAILED DESCRIPTION

Figure 1A:
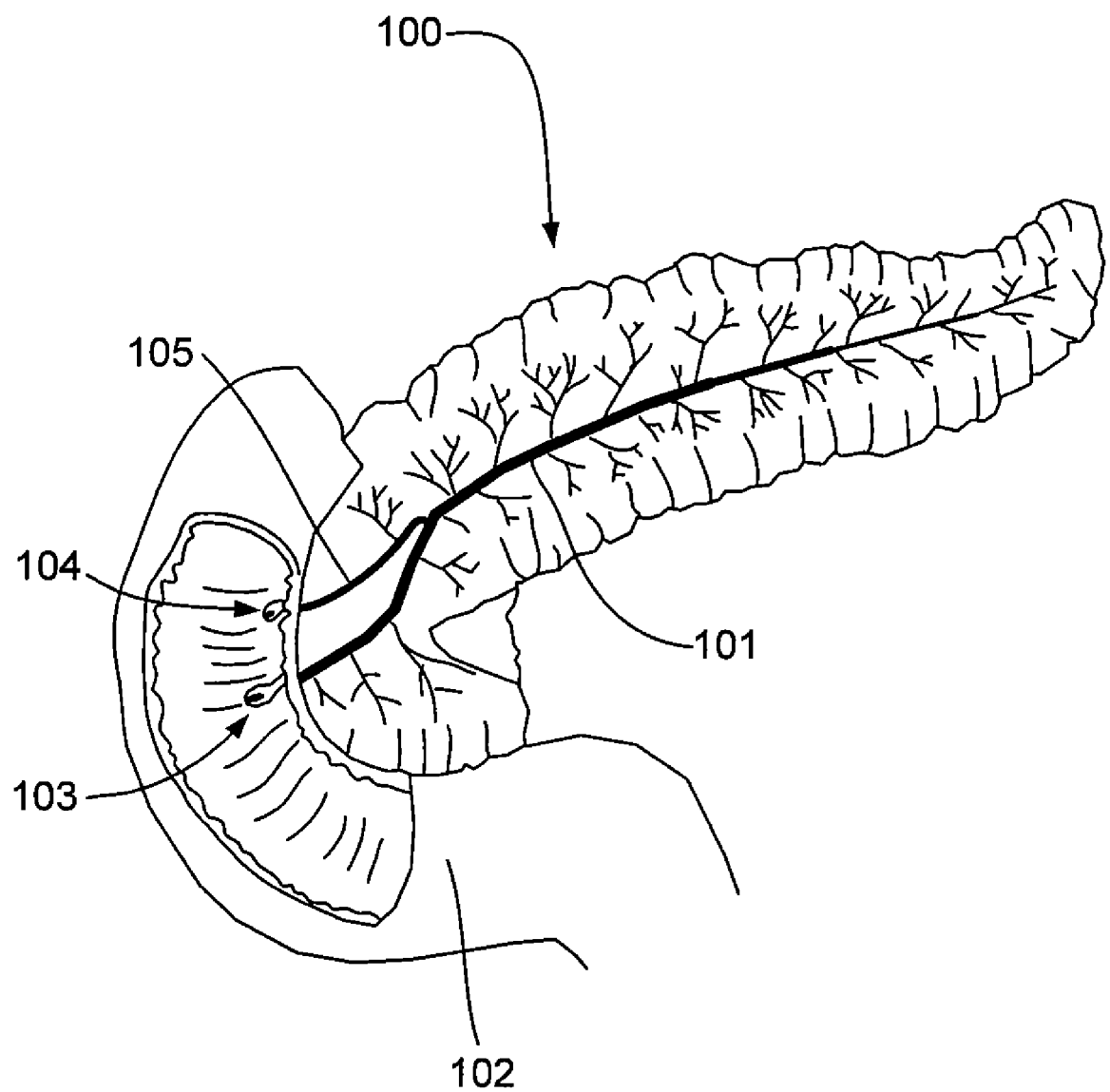
FIG. 1A is a front view of an exemplary human pancreas and a portion of the duodenum.

Methods and systems for treating a patient with ischemia pain are described herein. As used herein, "ischemia pain" refers to any type of pain caused by other otherwise associated with ischemia in one or more visceral organs. Ischemia pain may be caused by chronic pancreatitis, ductal hypertension, enzyme buildup, leakage, ductal occlusions or obstructions, inflammation, improper enzyme secretion, and/or any other dysfunction in a visceral organ.

In some examples, a stimulator may be configured to apply at least one stimulus to one or more stimulation sites in accordance with one or more stimulation parameters. The stimulus may be configured to treat visceral ischemia pain and may include electrical stimulation and/or drug stimulation. The stimulus may be used to decrease visceral ischemia pain due to conditions associated with chronic pancreatitis, including ductal hypertension, pancreatic enzyme buildup, pancreatic leakage, and ductal obstructions. As used herein, "treating" visceral ischemia pain refers to any amelioration or prevention of one or more causes, symptoms, and/or sequelae of pain resulting from or associated with ischemia in a visceral organ.

A number of advantages are associated with the systems and methods described herein. For example, the techniques used to implant the stimulator may be minimally invasive and carry a low risk of external scarring. The procedures described herein for treating ischemia pain may be reversible in that implanted devices may be turned off and/or removed at any time. Moreover, adjustments to the stimulation parameters may be made throughout the treatment period by reprogramming the implanted stimulator via, for example, a transcutaneous communication link.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Moreover, for illustrative purposes only, the exemplary methods and systems of the present specification are described in connection with ischemia pain caused by or related to chronic pancreatitis. It will be understood, however, that the present methods and systems may be applied to the treatment of ischemia pain in any of the visceral organs, including but not limited to the duodenum, small intestine, colon, liver, spleen, kidneys, adrenal glands, stomach, appendix, and/or gall bladder.

To facilitate an understanding of the exemplary systems and methods described herein, a brief overview of the etiology of pancreatitis and ischemia pain related to chronic pancreatitis will be given in connection with FIGS. 1A through 1C.

FIG. 1A is a front view of a human pancreas 100. As shown in FIG. 1A, the pancreas 100 is in direct contact with the duodenum 102, which is the first part of the small intestine and responsible for the breakdown of food within the small intestine. The pancreas 100 includes both endocrine and exocrine tissue. Endocrine tissue produces and secretes hormones such as insulin, glucagon, somatostatin, and others into the bloodstream level. Exocrine tissue produces and secretes into the duodenum 102 pancreatic juice containing enzymes (e.g., trypsin, chymotrypsin, and bicarbonate ions) that break down digestible foods within the digestive tract. As will be described in more detail below, pancreatitis and associated ischemia pain are often caused by pancreatic exocrine and endocrine dysfunction.

The exocrine tissue of the pancreas 100 includes a large number of ducts arranged in clusters referred to as acini. Pancreatic juices are first secreted into a lumen of each acinus. The juices accumulate within these ducts and eventually drain into a main duct known as the pancreatic duct 101. The pancreatic duct 101 empties into the duodenum 102 through a perforation known as the major duodenal papilla 103. Most people have only one main pancreatic duct 101, but in some cases a branch of the pancreatic duct 105 known as the accessory pancreatic duct (alternatively referred to as the Duct of Santorini) also empties into the duodenum 102 at a perforation called the minor duodenal papilla 104.

Pancreatitis is a painful condition in which the pancreas 100 becomes inflamed. Pancreatitis may be chronic or acute. As mentioned, one theory regarding the pathogenesis of chronic pancreatitis suggests that ductal occlusions in the exocrine tissue of the pancreas 100 do not permit the proper flow of pancreatic juices through the pancreatic duct 101 and duodenal papilla 103 and 104. This hindrance of the natural passage of pancreatic juices into the gastrointestinal tract may cause the pancreatic juices to build up within the pancreas 100, thus creating ductal distension, tissue damage, and pain. The increased pressure in the pancreatic duct 101 and other ducts, may induce tissue hypertension and ischemia.

Figure 1B:
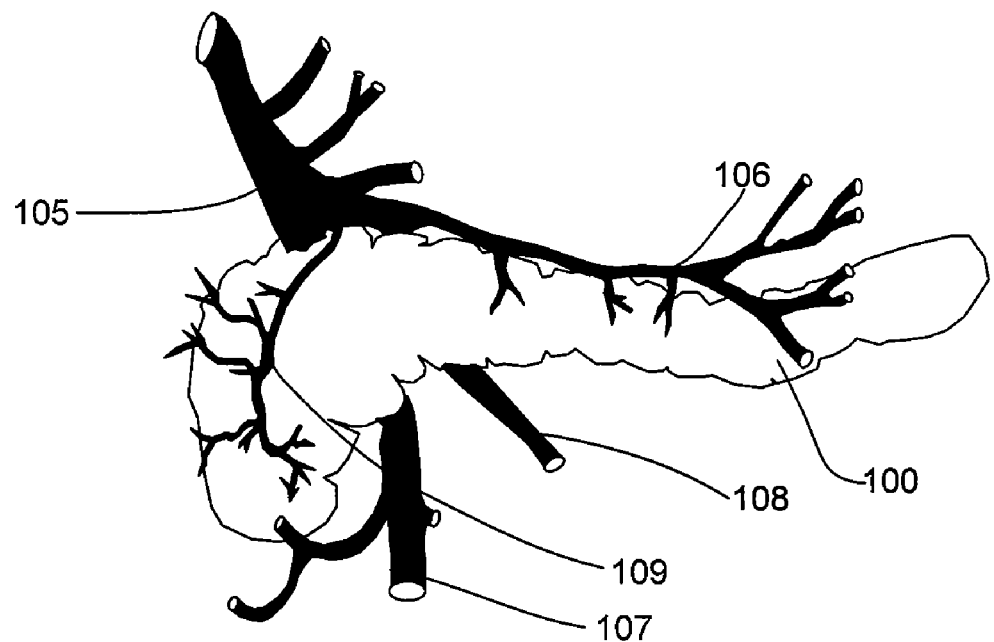
FIG. 1B is a front view of an exemplary pancreas and a partial view of the vascular tissue thereof.

FIG. 1B is a front view of the pancreas 100 showing a partial view of the vascular tissue thereof. Many of the blood vessels that return blood from the pancreas 100 to the heart are extensions of the portal vein 105. The splenic vein 106 (also known as the lienal vein) is one such extension that provides for the passage of blood through the pancreas 100. The superior mesenteric vein 107, inferior mesenteric vein 108, and pancreaticoduodenal vein 109 all channel blood into the portal vein 105, through which the blood is returned to the heart.

Figure 1C:
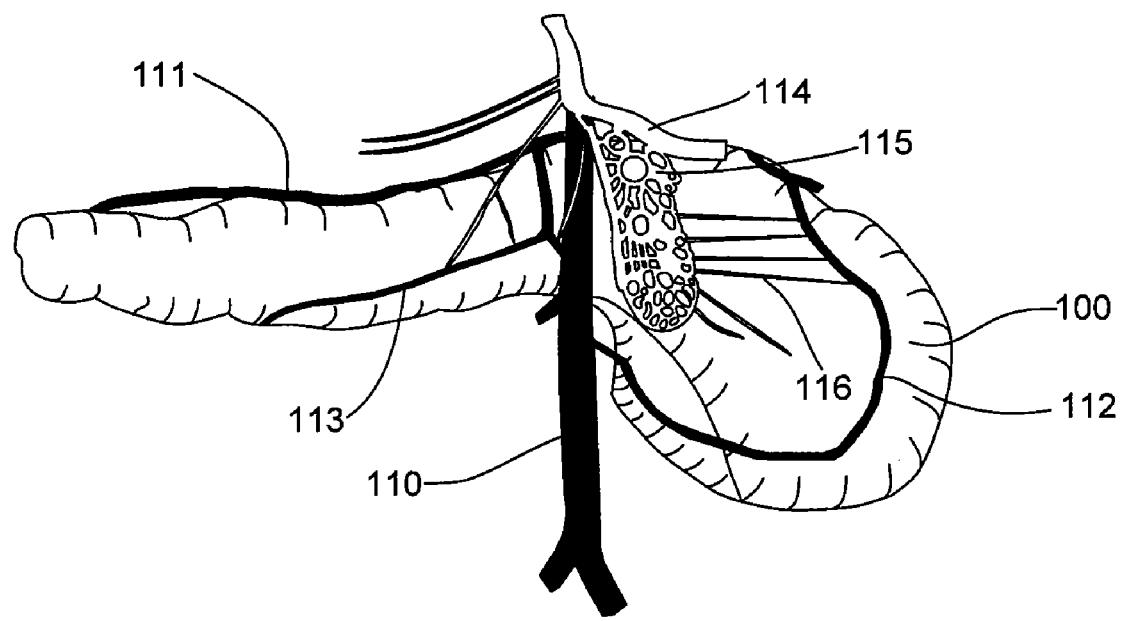
FIG. 1C is a dorsal view of an exemplary pancreas and a partial view of the vascular tissue and the innervation thereof.

FIG. 1C is a dorsal view of the pancreas 100 showing a partial view of vascular and neural tissue thereof. Many of the blood vessels that provide blood to the pancreas 100 from the heart are extensions and subextensions of the abdominal aorta. One such extension is the superior mesenteric artery 110, which feeds the splenic artery 111. The superior pancreaticoduodenal artery 112 and the inferior pancreaticoduodenal artery 113 are extensions of the gastroduodenal and hepatic arteries.

Many of the nerves that innervate the pancreas 100 extend from the distal end of the vagal trunk. The celiac trunk 114 is one such extension that innervates the pancreas. Neural tissue known as the celiac plexus 115 is located near where the celiac trunk 114, the superior mesenteric artery 110, and renal arteries branch from the abdominal aorta. Like other nerve plexuses, the celiac plexus 115 includes a network of interconnecting nerve fibers. The celiac trunk 114, the celiac plexus 115, nerve branches thereof (e.g., 116), and other neural tissue serve to innervate the pancreas 100. In particular, these nerves may innervate the exocrine tissue of the pancreas 100 and help regulate the exocrine functions of the pancreas 100.

It is believed that applying a stimulus to one or more stimulation sites within a patient may be useful in treating pain caused by ischemia in visceral organs. As used herein, the term "stimulation site" may refer to one or more regions of vascular tissue in and/or around an affected visceral organ and/or one or more nerves that innervate the vascular tissue of the affected visceral organ.

For example, in cases where ischemia pain in the pancreas is to be treated the stimulation site may include, but is not limited to, vascular and/or neural tissue such as the abdominal aorta, the splenic artery and vein, the portal vein, the hepatic artery, the gastroduodenal artery, the superior and inferior pancreaticoduodenal arteries, any other vascular tissue of the pancreas, one or more nerves that innervate vascular tissue of or extending from the pancreas, one or more nerves that innervate exocrine and/or endocrine tissue of the pancreas, the celiac trunk or branches thereof, one or more of the sympathetic or parasympathetic nerves surrounding or near the celiac trunk, the dorsal root ganglion, one or more dorsal columns and/or roots, the sympathetic trunk, the sympathetic ganglia, one or more levels of the spinal cord (e.g., C1-C4 and/or T4-L2), and/or one or more somatic nerves in or around the pancreas. Additionally or alternatively, the stimulation site may include exocrine tissue within the pancreas, endocrine tissue within the pancreas, and/or any other tissue of the pancreas as may suit a particular application.

In some examples, as will be described in more detail below, the stimulus may be configured to increase blood flow to or within the affected visceral organ to treat ischemia pain. For example, the stimulus may be applied to the spinal cord and/or vascular smooth muscle in and/or around the pancreas and configured to increase blood flow to the pancreas to treat ischemia pain associated with chronic pancreatitis. An increase in blood flow to the pancreas may treat ischemia pain by increasing pancreatic oxygenation, restoring proper tissue pH levels, and/or otherwise affecting the pancreas. In some examples, the stimulus may be configured to dilate a visceral organ's artery or vein affected by ischemia, thereby increasing the flow of blood through the artery or vein to the visceral organ.

Consequently, a stimulator may be implanted within a patient to deliver a stimulus to one or more of the stimulation sites described herein to treat ischemia pain. The stimulus may include an electrical stimulation current and/or the infusion of one or more therapeutic drugs at the stimulation site.

As used herein, and in the appended claims, the term "stimulator" will be used broadly to refer to any device that delivers a stimulus to a stimulation site to treat ischemia pain. Thus, the term "stimulator" includes, but is not limited to, a microstimulator, implantable pulse generator (IPG), spinal cord stimulator (SCS), external trial stimulator, system control unit, deep brain stimulator, drug pump, or similar device.

Figure 2:
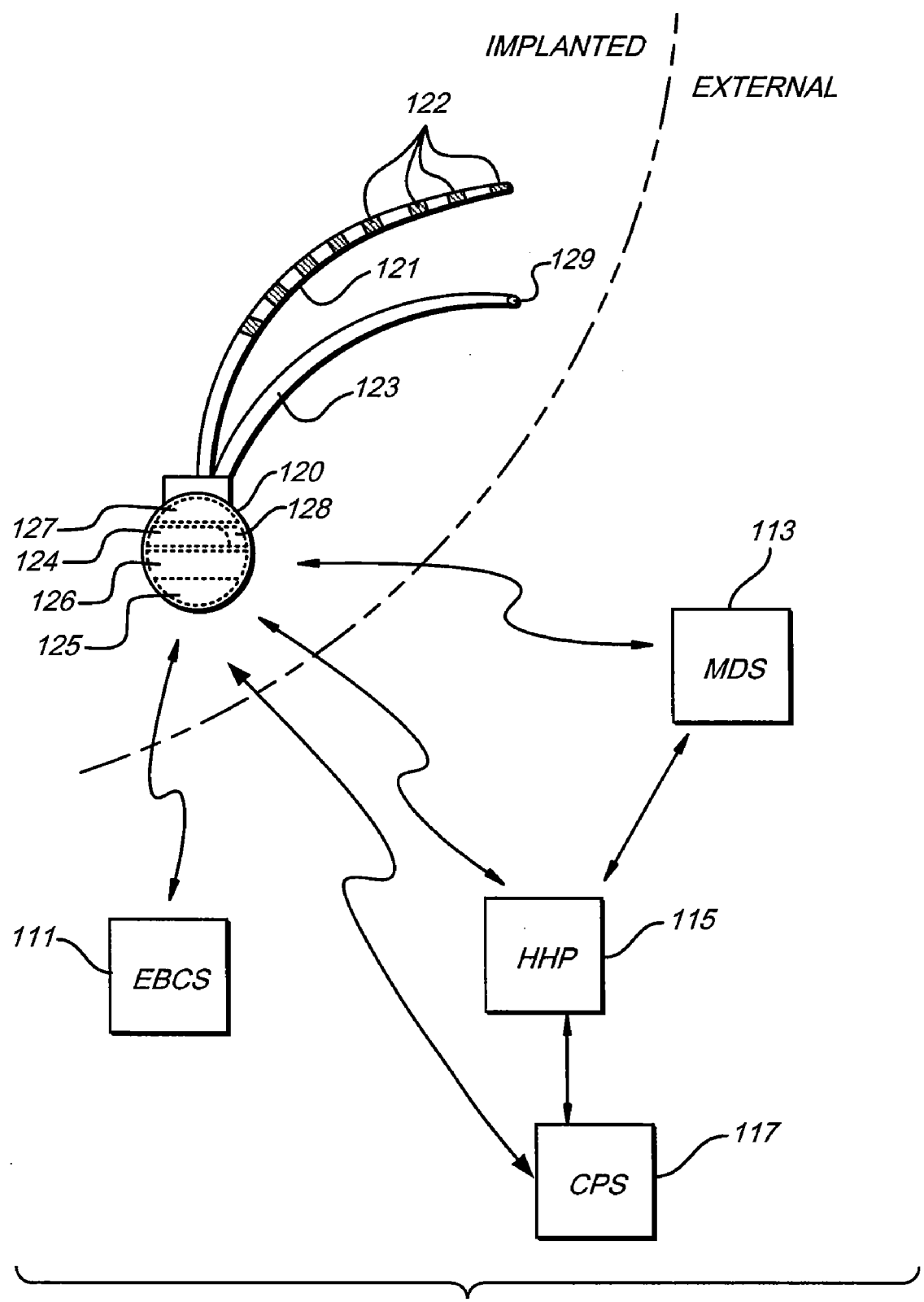
FIG. 2 illustrates an exemplary implantable stimulator according to principles described herein.

A more detailed description of an exemplary stimulator and its operation will now be given in connection with FIG. 2. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application. In some alternative examples, as will be described in more detail below, the stimulator 120 may be leadless.

As illustrated in FIG. 2, the stimulator 120 includes a number of components. It will be recognized that the stimulator 120 may include additional and/or alternative components as best serves a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607,843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 111 may be provided to generate power that is used to recharge the power source 125 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump may also be included within the stimulator 120. The pump may be configured to store and dispense one or more drugs, for example, through a catheter 123. The catheter 123 may be coupled at a proximal end to the stimulator 120 and may have an infusion outlet 129 for infusing dosages of the one or more drugs at the stimulation site. In some embodiments, the stimulator 120 may include multiple catheters 123 and/or pumps for storing and infusing dosages of the one or more drugs at the stimulation site.

The one or more drugs that may be applied to a stimulation site to treat ischemia pain may have a dilating effect on blood vessels, arteries, veins, and/or other vascular tissue in or around the affected organ to increase blood flow through the vascular tissue and decrease ischemia and hypertension. Exemplary vasodilation drugs that may be applied to the simulation site include, but are not limited to, at least one or more of the following: nitric oxide (NO), an endothelium-derived relaxing factor (EDRF), hydralazine, a calcium-channel antagonist, epoprostenol (prostacyclin), and/or other vasodilators.

Any of the drugs listed above, alone or in combination, or other drugs or combinations of drugs developed or shown to treat ischemia pain may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 may allow a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus.

Specific stimulation parameters may have different effects on different types, causes, or symptoms of ischemia pain. Thus, in some examples, the stimulation parameters may be adjusted at any time throughout the treatment course as best serves the particular patient being treated. It will be recognized that any of the characteristics of the stimulation current, including, but not limited to, the pulse shape, amplitude, pulse width, frequency, burst pattern (e.g., continuous or intermittent), duty cycle or burst repeat interval, ramp on time, and ramp off time may be adjusted throughout the course of treatment as best serves a particular application.

To illustrate, a baseline set of stimulation parameters may initially be set to begin treatment of ischemia pain. These baseline values may be adjusted throughout the course of treatment in response to patient feedback and/or sensed indicators of ischemia pain. Additionally or alternatively, the patient and/or clinician may adjust the stimulation parameters at any time to prevent accommodation, collateral stimulation, and/or ineffectiveness.

In some embodiments, the stimulation parameters may be configured to provide monopolar electrical stimulation. For example, an external case of the stimulator 120 may be used as an indifferent electrode. In other embodiments, the stimulation parameters may be configured to provide bipolar electrical stimulation (e.g., one of the electrodes 122 may be used as an indifferent electrode). Different stimulation parameters may have different effects on neural or other tissue. Therefore, parameters may be chosen to target specific neural or other tissue populations and/or exclude others in order to achieve a desired therapeutic effect. Additionally, the stimulation parameters may provide for current steering between electrodes 122 such that specific stimulation sites may be targeted.

As mentioned above, the stimulation site may include vascular tissue in or around an affected visceral organ and/or one or more nerves that innervate the vascular tissue. Stimulation current may cause the vascular tissue to become dilated or relaxed such that ischemia and pain associated with ischemia may be reduced. An exemplary baseline set of stimulation parameters that may be used to initially define stimulation current that is used to stimulate vascular tissue in or around an affected visceral organ includes, but is not limited, to the stimulation parameters shown in Table 1. It will be recognized that the baseline set of stimulation parameters shown in Table 1 may vary depending on the particular patient being treated and that additional or alternative stimulation parameters may be defined.

TABLE 1

Exemplary Baseline Stimulation Parameters

| | |
|---|---|
| Pulse width | 0.01 microseconds (μsec) - 5 milliseconds (msec) |
| Frequency | Greater than 100 Hertz (Hz) to inhibit tissue or less than or equal to 100 Hz to excite tissue |
| Amplitude | 0.01-15 milliamps (mA) |

Hence, as shown in Table 1, a stimulation current having a pulse width of 0.01 μsec-5 msec and an amplitude of 0.01-15 mA may be initially applied to vascular tissue in or around an affected visceral organ to treat ischemia pain associated with the visceral organ. The pulse width and amplitude may initially have relatively small values so as to avoid muscle spasms, nerve damage, or discomfort.

The frequency of the stimulation current may depend on the type of vascular tissue being targeted. For example, an excitatory frequency of less than 100 Hz may be applied to one or more parasympathetic nerves to increase blood flow to a visceral organ by dilating the blood vessels leading to the GI tract and other non-essential organs (e.g., the pancreas). An inhibitory frequency of 100 Hz or more may be applied to one or more sympathetic nerves to increase blood flow to a visceral organ by preventing diversion of blood flow away from the GI tract and non-essential organs (e.g., the pancreas). It will be recognized that the frequency of the stimulation current may vary as may serve a particular patient.

In some examples, these baseline parameters may be determined in the initial fitting session and may depend on the electrode placement (e.g., how proximal the electrodes are to the stimulation site), local impedance (which may be affected by scar tissue, etc.), and patient variability. The clinician or other programmer may make subtle, iterative adjustments to any of the stimulation parameters in response to real-time feedback from the patient.

After a predetermined length of time (e.g., a week, a month, or multiple months) of treatment or as the need may arise, the patient may be evaluated to determine whether the stimulation parameters need to be adjusted and/or whether the additional stimulation is needed in order to treat the ischemia pain. In some examples, if the patient no longer exhibits any symptoms of ischemia pain, the stimulation may be terminated. Alternatively, if it is determined that the patient needs further treatment, the stimulation may continue in accordance with the same set of stimulation parameters or in accordance with a newly defined set of stimulation parameters. For example, the stimulation parameters may be adjusted from the exemplary baseline stimulation parameters described previously in connection with Table 1 to have values that better suit the needs of the patient and more effectively treat ischemia pain.

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, or any other type of implantable device configured to deliver a stimulus to a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

The stimulator 120 of FIG. 2 may alternatively include a microstimulator. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
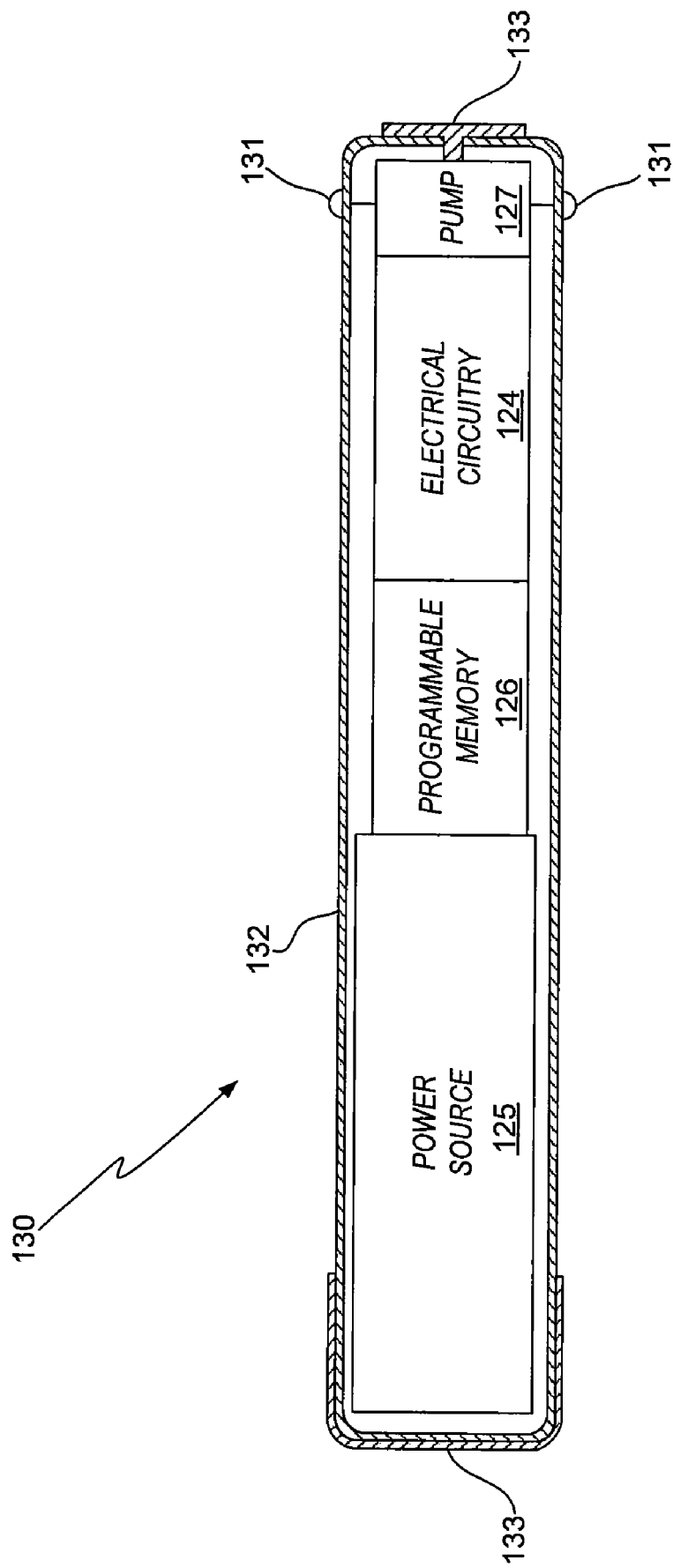
FIG. 3 illustrates an exemplary microstimulator according to principles described herein.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, and the pump 127 described in connection with FIG. 2. These components may be housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface thereof.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4A:
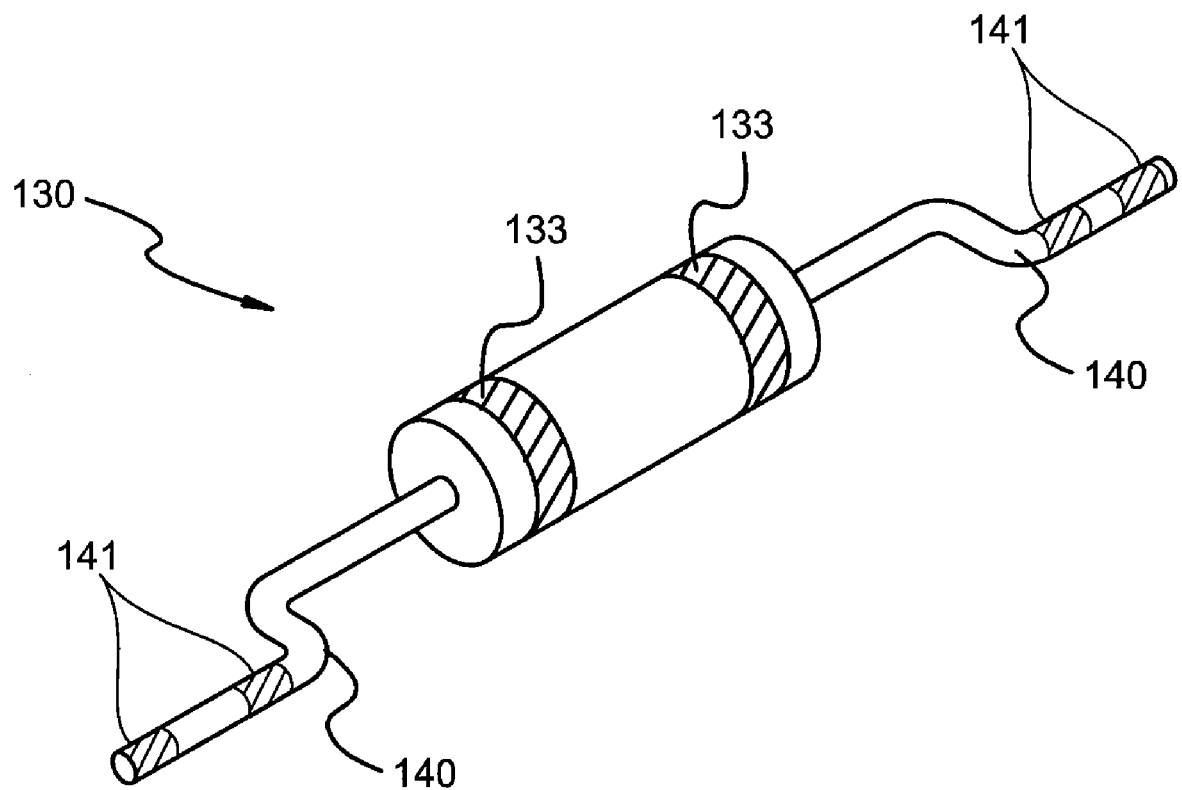
FIG. 4A shows an example of a microstimulator with one or more leads coupled thereto according to principles described herein.
Figure 4C:
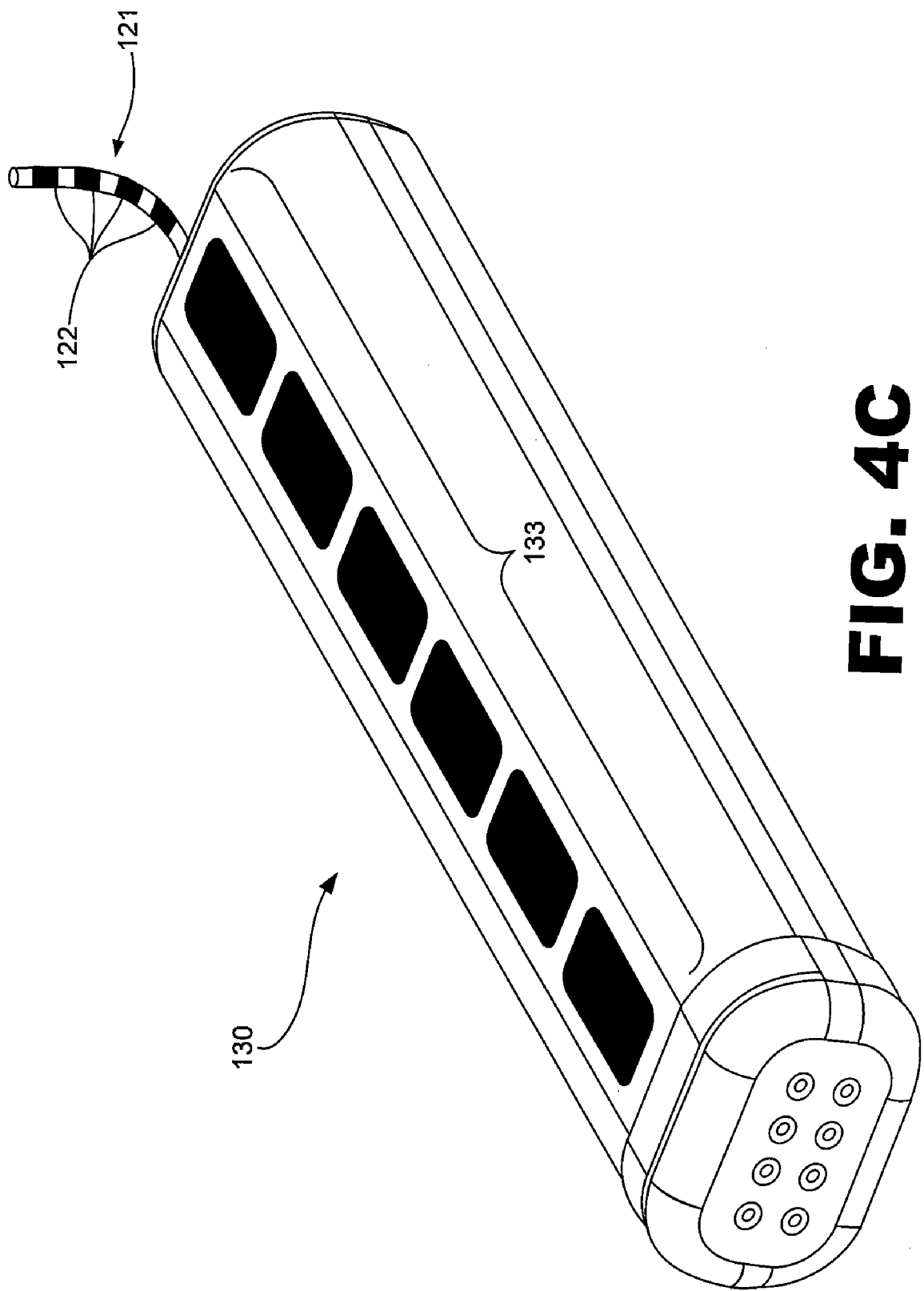
FIG. 4C shows the exemplary microstimulator of FIG. 4B coupled to a lead having a number of electrodes disposed thereon according to principles described herein.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 133 disposed on the outer surface thereof.

FIG. 4B illustrates an exemplary microstimulator 130 with a plurality of electrodes 133 disposed on an outer surface thereof. In some examples, any number of electrodes 133 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 133 and 122 may be selectively configured to serve as an anode or as a cathode.

Figure 5:
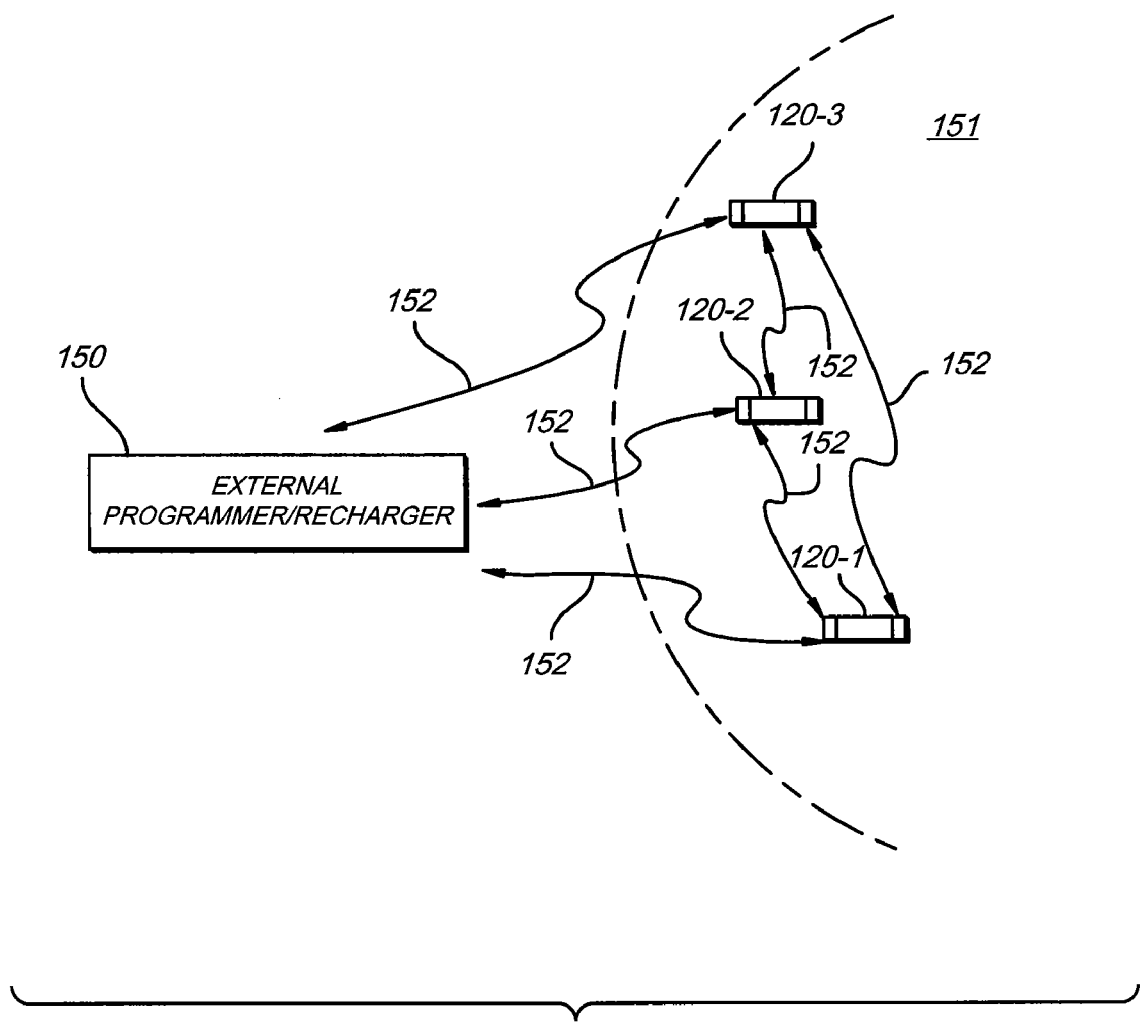
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the symptoms or causes of ischemia pain and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of ischemia pain, communicate or receive data regarding such indicators, and adjust stimulation parameters accordingly.

In order to determine the strength and/or duration of electrical stimulation and/or amount and/or type(s) of stimulating drug(s) required to most effectively treat ischemia pain, various indicators of ischemia pain and/or a patient's response to treatment may be sensed or measured. The stimulator 120 may then adjust the stimulation parameters (e.g., in a closed loop manner) in response to one or more of the sensed indicators. Exemplary indicators include, but are not limited to, neurotransmitter levels, user input (e.g., input from the patient, physician, clinician, and/or other user), circumference changes in vascular tissue, detected blood flow, a change in blood oxygenation, a change in blood pH levels, changes in hormone concentration, detected stomach activity, circumference changes in the duodenum (e.g., as a result of peristalsis), pyloric sphincter contraction, detected food passing through the gastrointestinal tract, sounds originating from the stomach or other location within the gastrointestinal tract (i.e., borborygmus), detected contraction of exocrine tissue around ductal occlusions, and pressure changes in the bile duct, pancreatic duct 101, ampulla, and/or duodenum 102. In some examples, the stimulator 120 may be configured to perform one or more of the measurements. Alternatively, other sensing devices may be configured to perform the measurements and transmit the measured values to the stimulator 120.

Examples of sensing devices that may be used as components of or in conjunction with the stimulator 120 include, but are not limited to, subcutaneous buttons (pressed by the user or a practitioner), hormonal or chemical sensors, piezoelectric sensors, strain gauges, optical sensors, pH detectors, auditory sensors, pressure sensors, and/or combinations thereof.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

By way of example, an exemplary method of treating ischemia pain may be carried out according to the following sequence of procedures. The steps listed below may be modified, reordered, and/or added to as best serves a particular application.

1. A stimulator 120 is implanted so that its electrodes 122 and/or infusion outlet 129 are in communication with a stimulation site within a patient. As used herein and in the appended claims, the term "in communication with" refers to the stimulator 120, stimulating electrodes 122, and/or infusion outlet 129 being adjacent to, in the general vicinity of, in close proximity to, directly next to, or directly on the stimulation site.

2. One or more stimulation parameters are configured to treat ischemia pain.

3. The stimulator 120 is programmed with the one or more stimulation parameters configured to treat ischemia pain. The stimulator 120 may then generate and apply at least one stimulus to the stimulation site in accordance with the stimulation parameters. The stimulus may include electrical stimulation, drug stimulation, gene infusion, chemical stimulation, thermal stimulation, electromagnetic stimulation, mechanical stimulation, and/or any other suitable stimulation.

4. When the patient desires to invoke stimulation, the patient sends a command to the stimulator 120 (e.g., via a remote control) such that the stimulator 120 delivers the prescribed stimulation to the stimulation site. For example, the stimulation may be activated by the patient when a particular incident of ischemia pain is detected. The stimulator 120 may alternatively or additionally be configured to apply the stimulation to the stimulation site in accordance with one or more pre-determined stimulation parameters and/or automatically apply the stimulation in response to sensed indicators of ischemia pain.

5. To cease stimulation, the patient may turn off the stimulator 120 (e.g., via a remote control).

6. Periodically, the power source 125 of the stimulator 120 is recharged, if necessary, in accordance with Function 1 described above.

In other examples, the treatment administered by the stimulator 120, i.e., drug therapy and/or electrical stimulation, may be automatic and not controlled or invoked by the patient. It will be recognized that the particular stimulation methods and parameters may vary as best serves a particular application.

Figure 6:
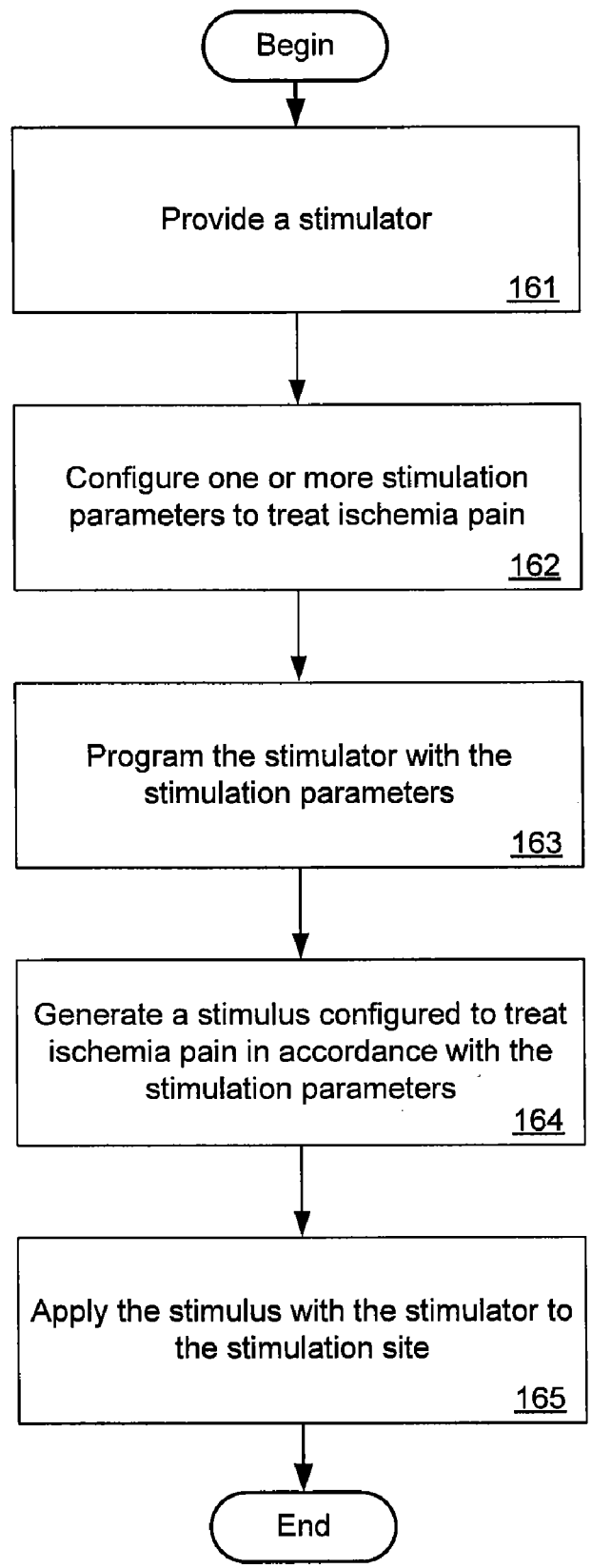
FIG. 6 is a flowchart of an exemplary method of treating ischemia pain in a visceral organ according to principles described herein.

FIG. 6 shows a flowchart of an exemplary method of treating ischemia pain, according to the principles that have been described in more detail above. While FIG. 6 illustrates exemplary steps according to one embodiment, other embodiments may omit, add to, reorder, and/or modify any of the steps shown in FIG. 6.

In step 161, a stimulator is provided. In step 162, one or more stimulation parameters are configured to treat ischemia pain. In step 163, the stimulator is programmed with the stimulator parameters. In step 164, a stimulus configured to treat ischemia pain in accordance with the stimulation parameters is generated. In step 165, the stimulus is applied with the stimulator to the stimulation site.

The stimulator 120 may be implanted within a patient using any suitable surgical procedure such as, but not limited to, small incision, open placement, laparoscopy, or endoscopy. Exemplary methods of implanting a microstimulator, for example, are described in U.S. Pat. Nos. 5,193,540; 5,312,439; 6,185,452; 6,164,284; 6,208,894; and 6,051,017. Exemplary methods of implanting an SCS, for example, are described in U.S. Pat. Nos. 6,487,446 and 6,516,227. Exemplary methods of implanting a deep brain stimulator, for example, are described in U.S. Pat. Nos. 6,016,449 and 6,539,263. All of these listed patents are incorporated herein by reference in their respective entireties.

To illustrate, FIGS. 7A-7D illustrate exemplary configurations wherein one or more electrodes 122 coupled to an implantable stimulator 120 have been implanted such that they are in communication with one or more stimulation sites within a patient. The configurations shown in FIGS. 7A-7D are merely illustrative of the many different implant configurations that may be used in accordance with the systems and methods described herein.

Figure 7A:
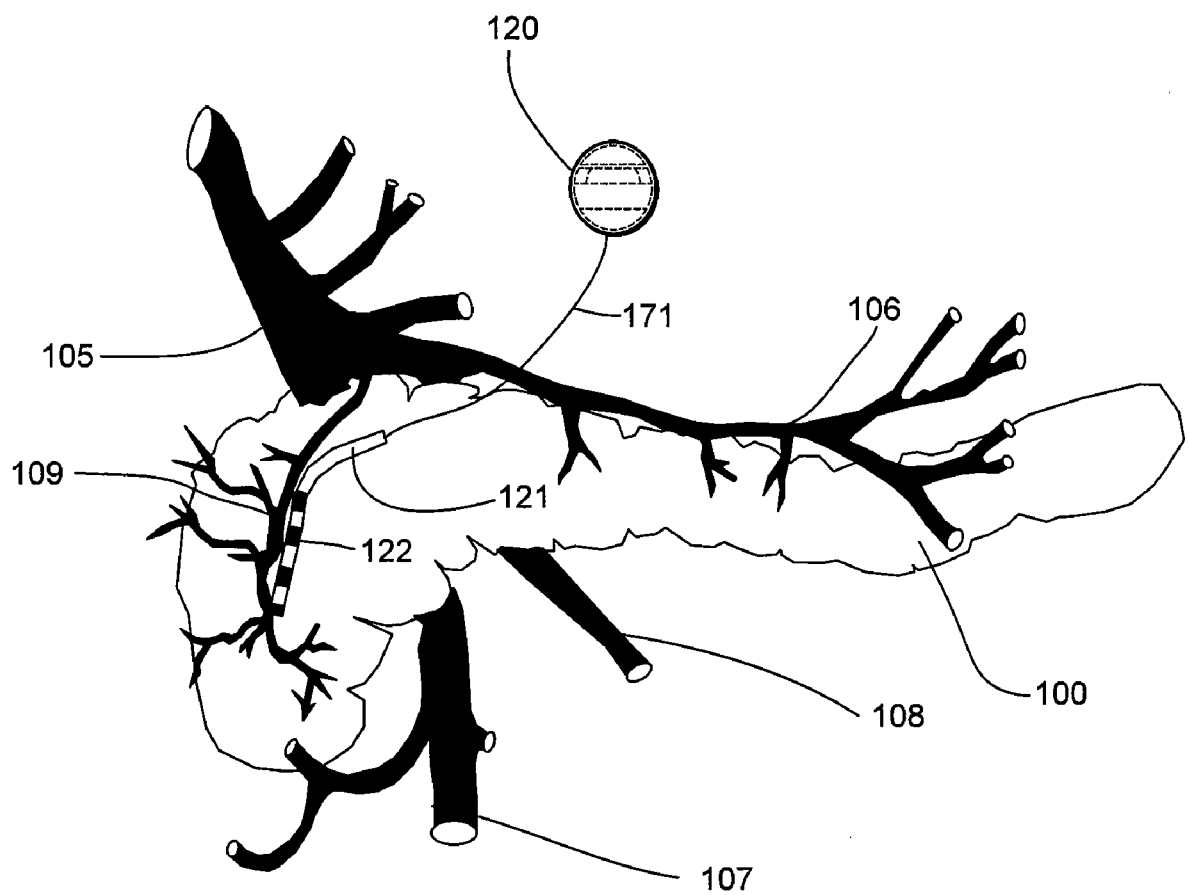
FIGS. 7A-7D illustrate exemplary configurations wherein one or more electrodes coupled to an implantable stimulator have been implanted such that they are in communication with one or more stimulation sites within a patient according to principles described herein.

In the example of FIG. 7A, the distal portion of a lead 121 having electrodes 122 disposed thereon may be placed along the surface of the pancreas 100 such that the electrodes 122 are in communication with one or more of the regions or vascular and/or other pancreatic tissue in the general vicinity of the pancreaticoduodenal vein 109 and/or one or more of the nerves that innervate the pancreaticoduodenal vein 109. It will be recognized that although only an electrode lead 121 is shown in FIG. 7A, a catheter 123 may additionally or alternatively be implanted for drug stimulation in a similar manner.

The lead 121 shown in FIG. 7A may be coupled to a stimulator 120 that has been implanted in a more convenient location with a lead extension 171. For example, the stimulator 120 may be subcutaneously implanted within the abdomen. This may allow easy access to the stimulator 120 and maximize the efficiency of power recharging and/or data communication operations between the stimulator 120 and an external instrument. Alternatively, the lead 121 may be coupled directly to the stimulator 120.

In some alternative examples, an appropriately sized stimulator 120 with one or more electrodes 122 disposed thereon may be implanted at least partially within the pancreas 100.

In some examples, an expanded ply(tetrafluoroethylene) (PTFE) sheet containing one or more electrodes may be attached to the surface of the pancreas 100. In this manner, a clot may be caused to form between the electrode array and the pancreas 100 so as to secure the electrodes at desired positions within the pancreatic tissue.

Figure 7B:
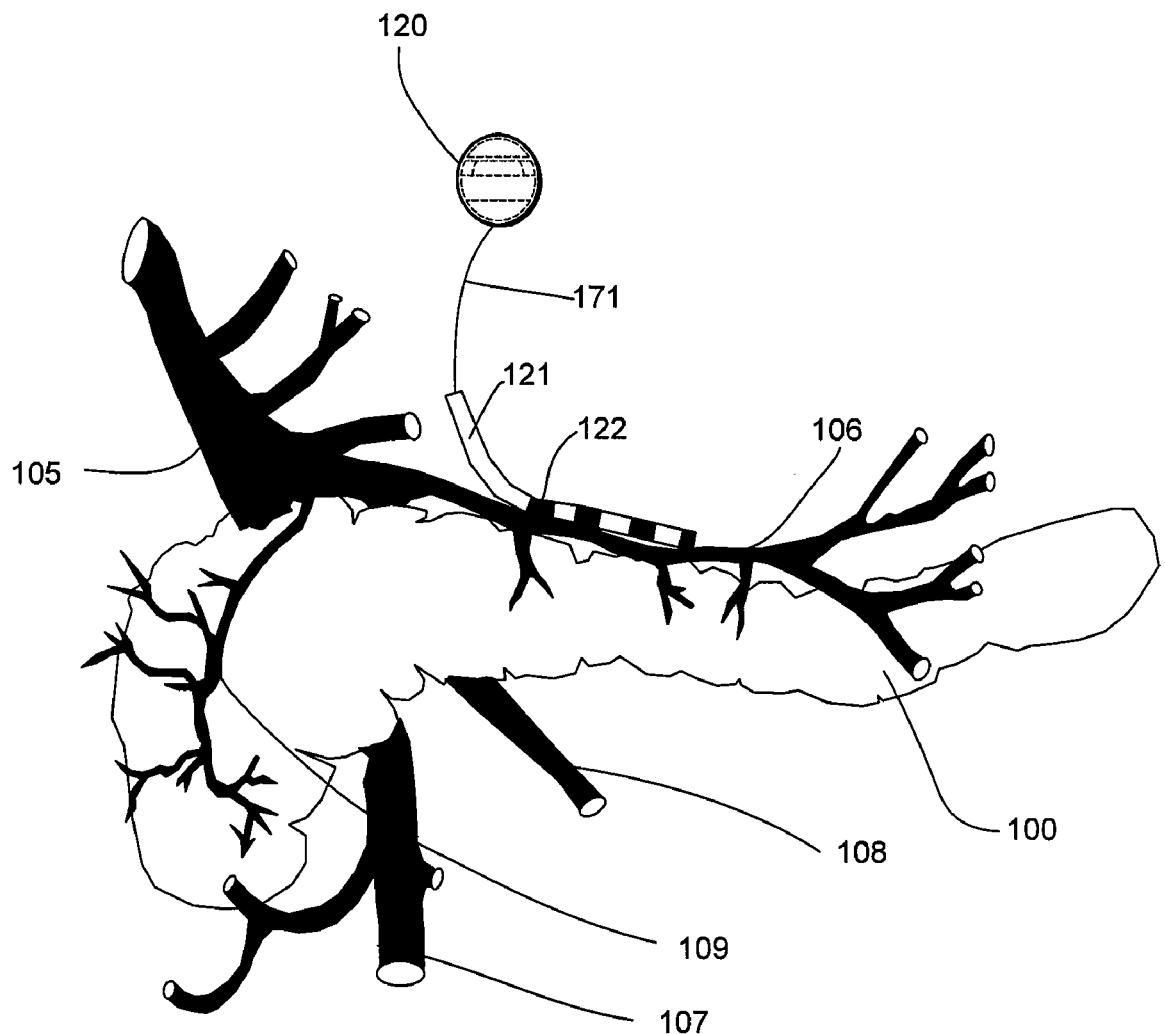

FIG. 7B shows a lead 121 having electrodes 122 disposed thereon placed at or near the tissue in the general vicinity of the splenic vein 106. Stimulation current from a stimulator 120 and applied via the electrodes 122 may be used to dilate the splenic vein 106, thus allowing for increased blood flow through the splenic vein 106, which may alleviate pain associated with pancreatic ischemia.

Figure 7C:
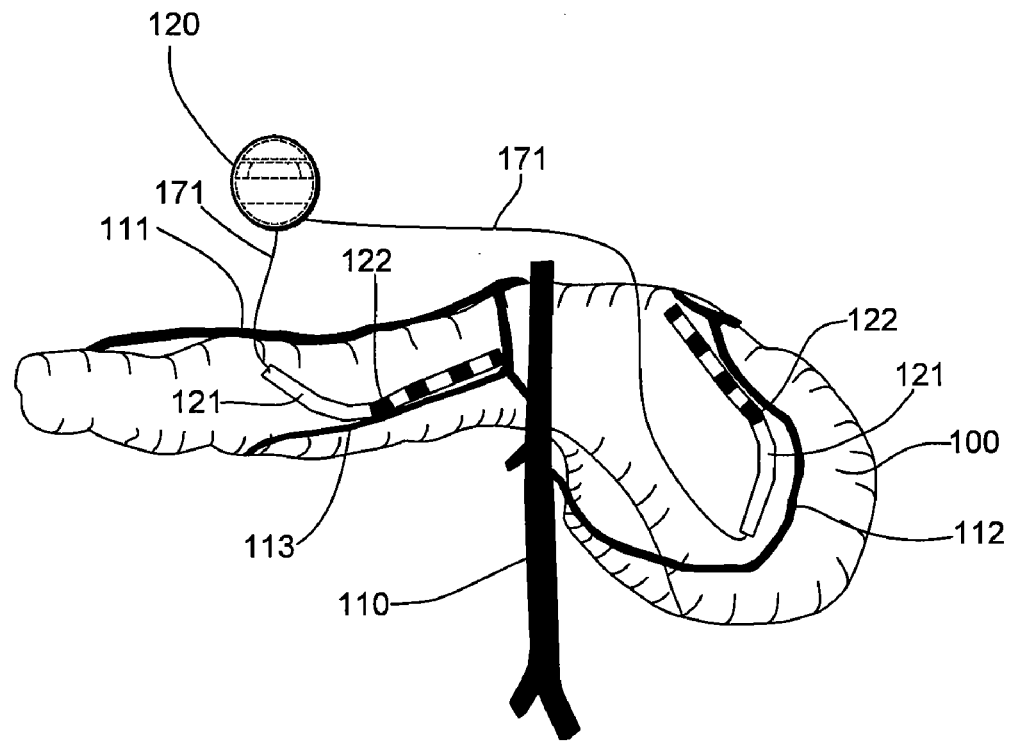

FIG. 7C shows two separate electrode leads 121 having electrodes 122 disposed at or near the tissue in the general vicinity of the superior pancreaticoduodenal artery 112 and the inferior pancreaticoduodenal artery 113. The electrode leads 121 of FIG. 7C may be coupled to a common stimulator 120. Alternatively, the electrode leads 121 may be coupled to separate stimulators 120. In this manner, electrical stimulation may be applied via one or both of the leads 121 in order to treat ischemia pain.

Figure 7D:
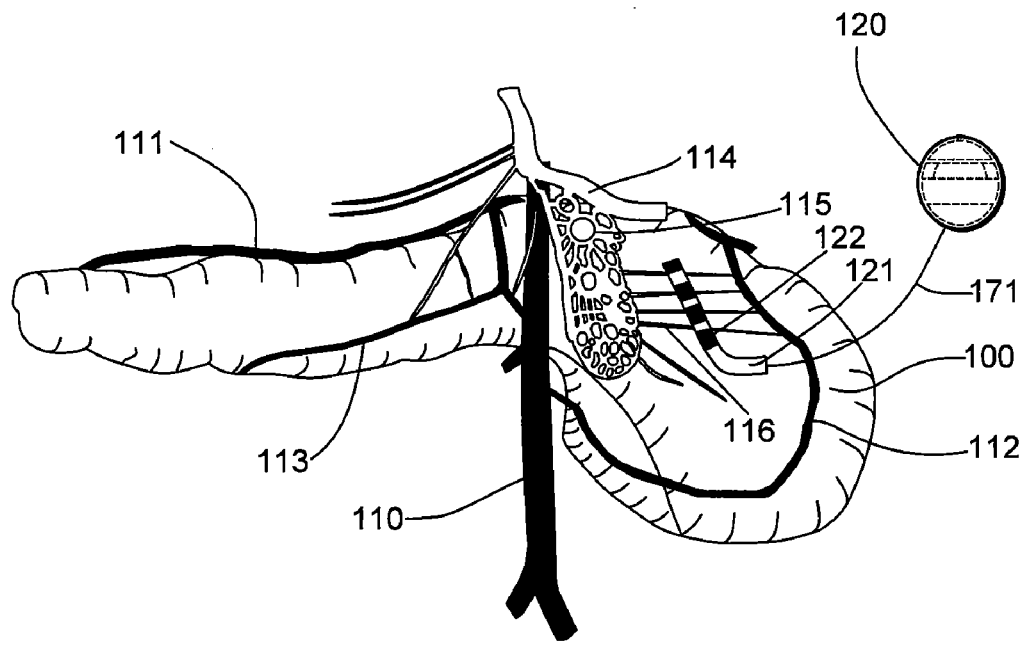

FIG. 7D shows an electrode lead 121 placed at nerve branches of the celiac plexus 115 and/or celiac trunk 114 that innervate regions of the pancreas 100, particularly the superior pancreaticoduodenal artery 112. A stimulator 120 may provide stimulation current to the electrodes via electrical connection 175. It will be understood that the lead 121 and/or stimulator 120 may be implanted at any other suitable stimulation site as may serve a particular application.

Figure 8:
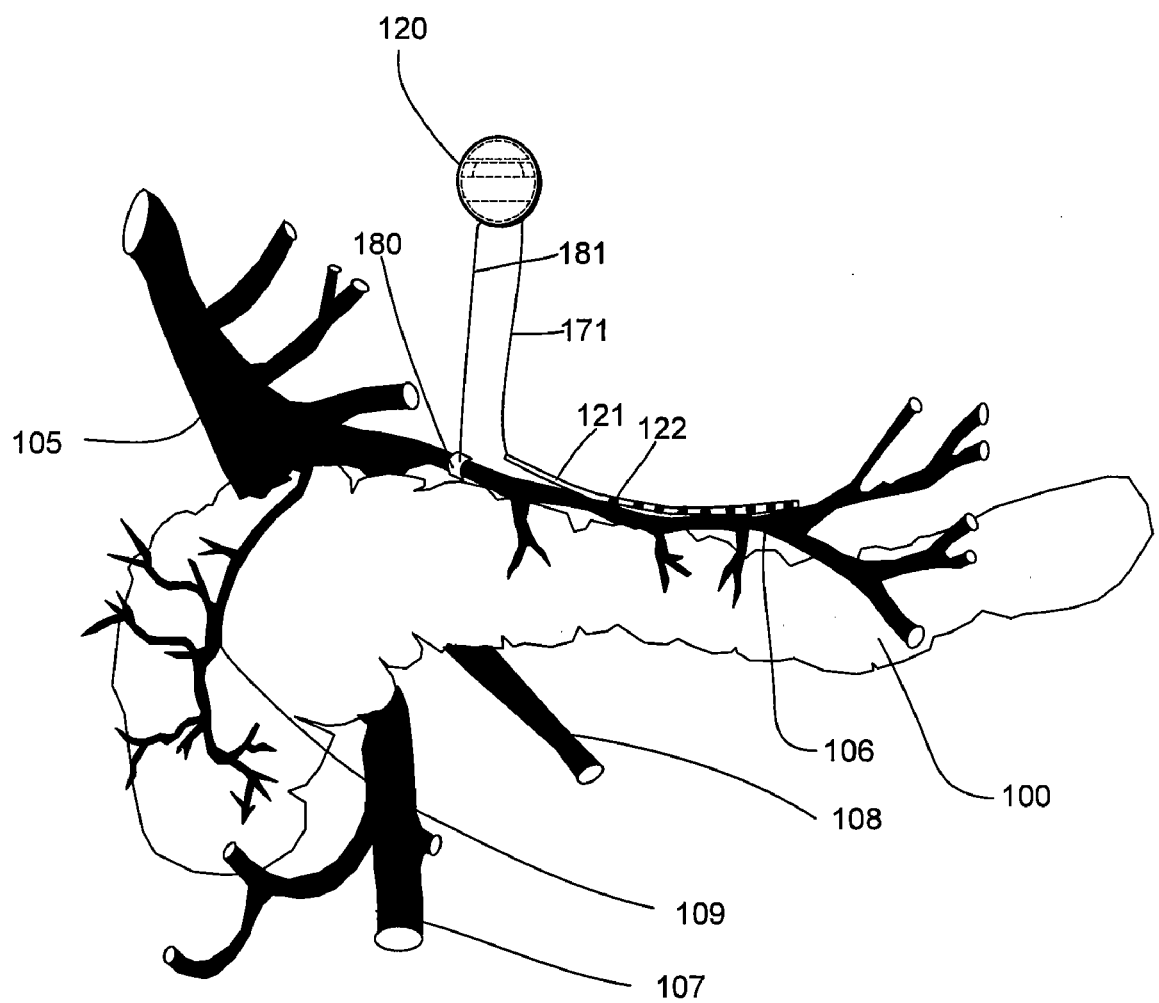
FIG. 8 illustrates an exemplary configuration wherein a sensing device is implanted within a patient and communicatively coupled to a stimulator according to principles described herein.

FIG. 8 illustrates an exemplary configuration wherein a sensing device 180 may be implanted within the patient and communicatively coupled to the stimulator 120. As shown in FIG. 8, a lead 121 having electrodes 122 may be disposed at a stimulation site within the patient (e.g., along a surface of splenic vein 106). The sensing device 180 may also be coupled to the splenic vein 106, for example, or to any other tissue within the patient. The sensing device 180 may be communicatively coupled to the stimulator 120 via any type of communication link 181 as may serve a particular application. The stimulator 120 may include electrical circuitry configured to interpret biological parameters detected by the sensing device 180 and use the sensed parameters to determine optimal stimulation parameters.

The sensing device 180 shown in FIG. 8 may include any type of sensing device described herein. For example, the sensing device 180 may include a strain gauge or piezoelectric element configured to measure changes in the circumference of the splenic vein 106.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with ischemia pain, comprising:
   providing a stimulator;
   configuring one or more stimulation parameters to treat ischemia pain in a visceral organ, wherein said visceral organ comprises at least one or more of a pancreas, a duodenum, a small intestine, a colon, a liver, a spleen, a kidney, an adrenal glands, a stomach, an appendix, and a gall bladder;
   programming said stimulator with said one or more stimulation parameters;
   generating a stimulus configured to treat said ischemia pain with said stimulator in accordance with said one or more stimulation parameters; and
   applying said stimulus with said stimulator to a stimulation site within said patient;
   wherein said stimulation site comprises at least one or more of a vascular tissue of said visceral organ and a nerve innervating said vascular tissue of said visceral organ.

2. The method of claim 1, wherein said stimulation site comprises at least one or more of an aorta, a nerve innervating said aorta, a celiac trunk, a spinal cord level, a splenic artery, a nerve innervating said splenic artery, a splenic vein, a nerve innervating said splenic vein, a portal vein, a nerve innervating said portal vein, a hepatic artery, a nerve innervating said hepatic artery, a gastroduodenal artery, a nerve innervating said gastroduodenal artery, a superior mesenteric artery, a nerve innervating said superior mesenteric artery, a superior mesenteric vein, a nerve innervating said superior mesenteric vein, a pancreaticoduodenal artery, a nerve innervating said pancreaticoduodenal artery, a blood vessel associated with said visceral organ, and a nerve innervating said blood vessel.

3. The method of claim 1, wherein said stimulus is configured to induce dilation of said vascular tissue.

4. The method of claim 1, wherein said stimulator is coupled to one or more electrodes, and wherein said stimulus comprises a stimulation current delivered via said electrodes.

5. The method of claim 1, wherein said stimulus comprises an infusion of one or more drugs at said stimulation site.

6. The method of claim 1, wherein said ischemia pain is associated with pancreatitis.

7. The method of claim 1, further comprising sensing at least one indicator related to said ischemia pain and using said at least one sensed indicator to adjust one or more of said stimulation parameters.

8. The method of claim 7, wherein said indicator comprises at least one or more of a neurotransmitter level, a user input, a circumference change in vascular tissues, a detection of blood flow, a change in blood oxygenation, a change in pH, a change in hormone concentration, a detected stomach activity, a circumference change in a duodenum, a pyloric sphincter contraction, a detection of food passing through the gastrointestinal tract, a change in pH, a sound, a contraction of exocrine tissue, a pressure change in a bile duct, a pressure change in a pancreatic duct, a pressure change in an ampulla, and a pressure change in a duodenum.

9. The method of claim 7, further comprising sensing said at least one indicator with at least one or more of a patient feedback sensor, a hormonal sensor, a chemical sensor, a piezoelectric sensor, a strain gauge, an optical sensor, a pH sensor, an auditory sensor, and a pressure sensor.

10. A method of treating ischemia pain, said method comprising:
- implanting a stimulator at least partially within a patient;
- configuring one or more stimulation parameters to treat ischemia pain in a visceral organ, wherein said visceral organ comprises at least one or more of a pancreas, a duodenum, a small intestine, a colon, a liver, a spleen, a kidney, an adrenal glands, a stomach, an appendix, and a gall bladder;
- programming said stimulator with said one or more stimulation parameters;
- generating a stimulation current configured to treat said ischemia pain with said stimulator in accordance with said one or more stimulation parameters; and
- applying said stimulation current with said implanted stimulator to a stimulation site within said patient;
- wherein said stimulation site comprises at least one or more of a vascular tissue of said visceral organ and a nerve innervating said vascular tissue of said visceral organ.

11. The method of claim 10, wherein said stimulation site comprises at least one or more of an aorta, a nerve innervating said aorta, a celiac trunk, a spinal cord level, a splenic artery, a nerve innervating said splenic artery, a splenic vein, a nerve innervating said splenic vein, a portal vein, a nerve innervating said portal vein, a hepatic artery, a nerve innervating said hepatic artery, a gastroduodenal artery, a nerve innervating said gastroduodenal artery, a superior mesenteric artery, a nerve innervating said superior mesenteric artery, a superior mesenteric vein, a nerve innervating said superior mesenteric vein, a pancreaticoduodenal artery, a nerve innervating said pancreaticoduodenal artery, a blood vessel associated with said visceral organ, and a nerve innervating said blood vessel.

12. The method of claim 10, wherein said stimulus is configured to induce dilation of said vascular tissue.

13. The method of claim 10, further comprising sensing at least one indicator related to said ischemia pain and using said at least one sensed indicator to adjust one or more of said stimulation parameters.

14. The method of claim 13, wherein said indicator comprises at least one or more of a neurotransmitter level, a user input, a circumference change in vascular tissues, a detection of blood flow, a change in blood oxygenation, a change in pH, a change in hormone concentration, a detected stomach activity, a circumference change in a duodenum, a pyloric sphincter contraction, a detection of food passing through the gastrointestinal tract, a change in pH, a sound, a contraction of exocrine tissue, a pressure change in a bile duct, a pressure change in a pancreatic duct, a pressure change in an ampulla, and a pressure change in a duodenum.

15. The method of claim 14, further comprising sensing said at least one indicator with at least one or more of a patient feedback sensor, a hormonal sensor, a chemical sensor, a piezoelectric sensor, a strain gauge, an optical sensor, a pH sensor, an auditory sensor, and a pressure sensor.

16. A system for treating a patient with ischemia pain, said system comprising:
- a stimulator configured to generate at least one stimulus in accordance with one or more stimulation parameters adjusted to treat ischemia pain in a visceral organ, wherein said visceral organ comprises at least one or more of a pancreas, a duodenum, a small intestine, a colon, a liver, a spleen, a kidney, an adrenal glands, a stomach, an appendix, and a gall bladder;
- a programmable memory unit in communication with said stimulator and programmed to store said one or more stimulation parameters to at least partially define said stimulus such that said stimulus is configured to treat said ischemia pain; and
- means, operably connected to said stimulator, for applying said stimulus to a stimulation site within said patient;
- wherein said stimulation site comprises at least one or more of a vascular tissue of said visceral organ and a nerve innervating said vascular tissue of said visceral organ.

17. The system of claim 16, wherein said means for applying said at least one stimulus comprises one or more electrodes, and wherein said stimulus comprises a stimulation current delivered via said electrodes.

18. The system of claim 16, further comprising a sensor operably connected to said stimulator.

19. The system of claim 16, wherein said stimulus is configured to induce dilation of said vascular tissue.

* * * * *